(12) United States Patent  
Guthrie et al.

(10) Patent No.: US 9,709,459 B1
(45) Date of Patent: Jul. 18, 2017

(54) MULTIPLE ENERGETIC PENETRATION AND DAMAGE PROGRESSION SENSOR

(71) Applicants: Michael J. Guthrie, Huntsville, AL (US); Michael C. Zari, Madison, AL (US)

(72) Inventors: Michael J. Guthrie, Huntsville, AL (US); Michael C. Zari, Madison, AL (US)

(73) Assignee: FREENT TECHNOLOGIES, Inc., Huntsville, AL (US)

( * ) Notice: Subject to any disclaimer, the term of this patent is extended or adjusted under 35 U.S.C. 154(b) by 155 days.

(21) Appl. No.: 14/664,638

(22) Filed: Mar. 20, 2015

Related U.S. Application Data (60) Provisional application No. 61/929,409, filed on Jan. 20, 2014.

(51) Int. Cl.
| | | |
|---|---|---|
| *G01M 11/08* | (2006.01) | |
| *G01M 5/00* | (2006.01) | |
| *G01N 3/30* | (2006.01) | |
| *G01N 3/313* | (2006.01) | |
| *G01D 5/26* | (2006.01) | |

(Continued)

(52) U.S. Cl.
CPC ........... *G01M 11/085* (2013.01); *F41H 1/02* (2013.01); *G01D 5/26* (2013.01); *G01L 5/0052* (2013.01); *G01M 5/0033* (2013.01); *G01M 5/0091* (2013.01); *G01N 3/30* (2013.01); *G01N 3/313* (2013.01)

(58) Field of Classification Search
CPC ........... G01M 11/085; G01M 5/0033; G01M 5/0091; F41J 5/04; F41J 5/041; F41J 5/044; F41J 5/048; F41J 5/02; F41J 5/06; F41J 5/00; G01V 8/16; G01V 8/24; G01B 7/004; G01B 11/18; F41H 1/02; G01D 5/353; G01D 5/26; G01D 5/268; G01N 3/30; G01N 3/313; G01L 1/24; G01L 1/242; G01L 1/243; G01L 1/245; G01L 5/0052

USPC ......... 250/221, 227.11, 216, 227.15, 227.16, 250/227.28; 385/14; 340/436, 437, 600, 340/665, 3.43

See application file for complete search history.

(56) References Cited

U.S. PATENT DOCUMENTS

| | | |
|---|---|---|
| 4,781,056 A | 11/1988 | Noel et al. |
| 4,836,030 A | 6/1989 | Martin |

(Continued)

*Primary Examiner* — Que T Le
*Assistant Examiner* — Jennifer Bennett
(74) *Attorney, Agent, or Firm* — Mark Clodfelter (57) ABSTRACT

A multiple energetic penetration and damage progression sensor is disclosed. A grid of sensing lines, such as passive optical fibers, is formed by laying the sensing lines in a crossing pattern to form a 2-Dimensional or 3-Dimensional coordinate grid. Signal receivers such as photo-detectors are connected to one or both ends of the sensing lines, and a data processor interprets received signals. When an impact or energetic penetration occurs at a location on or near a sensing line, energy passes down the sensing line in both directions away from the point of impact or penetration. Each pair of "X-Y" or "X-Y-Z" recordings from receivers receiving the energy is processed to determine a location, penetration volume and progression in time of the impact or penetration. This sensor can be made conformal to any regular and continuous surface geometry, volume geometry, or surfaces or volumes of physical objects of interest.

18 Claims, 7 Drawing Sheets

(51) Int. Cl.
*G01L 5/00* (2006.01)
*F41H 1/02* (2006.01)

(56) References Cited

U.S. PATENT DOCUMENTS

| | | |
|---|---|---|
| 5,013,908 A | 5/1991 | Chang |
| 5,015,842 A | 5/1991 | Fradenburgh et al. |
| 5,072,110 A | 12/1991 | Lu et al. |
| 6,559,437 B1 | 5/2003 | Pope et al. |
| 6,841,766 B2 | 1/2005 | Gauthier, Jr. et al. |
| 6,931,166 B2 | 8/2005 | Gauthier, Jr. et al. |
| 7,156,559 B2 | 1/2007 | Gauthier, Jr. et al. |
| 7,189,959 B1 | 3/2007 | Morison et al. |
| 7,197,197 B2 | 3/2007 | Gauthier, Jr. et al. |
| 7,406,219 B2 | 7/2008 | Gauthier |
| 7,435,010 B2 | 10/2008 | Gauthier, Jr. et al. |
| 7,609,156 B2 * | 10/2009 | Mullen ............... F41G 3/147 2/455 |
| 7,921,727 B2 * | 4/2011 | Rice .................... G01B 7/18 73/762 |
| 8,316,690 B1 * | 11/2012 | Kiefer .................. G01M 7/00 73/12.01 |
| 2004/0120684 A1 * | 6/2004 | Ishibashi ............ C09K 11/7734 385/141 |
| 2004/0206187 A1 | 10/2004 | Williams |
| 2004/0256543 A1 | 12/2004 | Ishihara |
| 2006/0180380 A1 | 8/2006 | Munch et al. |
| 2006/0278240 A1 | 12/2006 | Spillman et al. |
| 2006/0291767 A1 | 12/2006 | Andrews et al. |

\* cited by examiner

MULTIPLE ENERGETIC PENETRATION AND DAMAGE PROGRESSION SENSOR

CROSS REFERENCE TO RELATED APPLICATION

This application claims the benefit of Applicant's U.S. provisional application No. 61/929,409, filed Jan. 20, 2014, titled "HIGH-VELOCITY IMPACT MULTIPLE-HIT (HIM-D) DETECTION SYSTEM, which is incorporated herein in its entirety by reference.

STATEMENT REGARDING FEDERALLY FUNDED DEVELOPMENT

This invention was made with government assistance from the Missle Defense Agency under SBIR Topic MDA13-015: Advanced Hit Detection systems Contract Number: HQ147-14-C-7830. The government has certain rights in the invention.

FIELD OF THE INVENTION

The present invention relates generally to high speed impact detection, and more particularly to a multiple energetic surface or volume penetration and damage progression sensor, or lower energy contact sensor. A grid of fiber-optic lines and mated photo-detectors measure initial and subsequent points of impactor penetration and damage progression due to multiple energetic penetrations of a surface or volume. Data is generated from detected light radiation originating from hot and energetically excited ends of severed optical fibers during penetration. In other embodiments, the optical fibers can be replaced with other types of lines employing other phenomenologies to either sense energetic impacts, or less energetic contacts.

BACKGROUND OF THE INVENTION

In aerospace, defense, energy production, and energetic materials applications it is often of interest to measure the precise location of energetic penetration or rupture of a surface or volume of interest. It is also of interest to characterize the impact if possible. In these and other applications it is often of interest to measure a precise location of contact between impacting or colliding bodies.

This invention has application to any field that requires local damage site characterization from energetic impacts, fire or high-temperature failure modes, explosive devices, munitions development, structure blast survivability studies, energetic propellant characterization, or surface damage due to extreme environments, such as occur in a detonation of an explosive or with space vehicles re-entering the Earth's atmosphere. Other applications include aircraft and building fire detection, rocket booster failure detection, and combat vehicle damage detection, location, and notification. Satellite and space station damage due to meteorite impacts is another application. For lower energetic encounters, an adaptation employing different low energy sensing modalities can enable non-destructive contact sensing as opposed to impact or penetration sensing.

U.S. Government agencies, such as the Missile Defense Agency (MDA), have interests in such technology in the field of missile defense where it is desired to destroy incoming enemy missiles. It is important to know the impact point or the multiple impact points that may occur in an interceptor engagement as well as the progression of the resulting damage through the particular target of interest. Tactical weapon lethality testing by the U.S. Army, Air Force, and Navy also requires knowledge of the hit-point on a particular target such as an armored vehicle, aircraft, ship, submarine, or bunker. Additionally, the National Aeronautics and Space Administration (NASA) has interest in damage assessment due to high-velocity impacts of debris and meteorites on space vehicles, as well as detection and location of potential burn-through and catastrophic failure of rocket boosters.

There are a number of existing hit-point electrical and optical sensor systems, which can either detect or estimate the location of an energetic penetration of surfaces. Optical systems include conventional optical grids and similar approaches such as the Break Detection System (U.S. Pat. No. 5,013,908 to Chang), which uses a grid of fiber optic cables as a detection system. It is important to note that this system is an "active" sensing system, requiring injection of an optical and modulated signal to continuously power an unbroken grid, so as to sense location of a broken optical conductor upon breakage from a penetration. A first drawback of using electrical detection techniques as above is that they are more complex since optical signals must be developed by electrical or RF power sources for each sensing line. This adds complexity and expense to the system. A second drawback is that the added complexity of these same electrical or RF power sources reduces the reliability of the system since if the source is inoperable, so too is the at least that line of the system. A third drawback of such systems is that during energetic events, electronics of the system often are disrupted by electromagnetic interference (EMI) that can cause corruption of the data. A further drawback is that, at least in the Chang reference, only location is detected, with no reference to timing. Yet another drawback is that no detection of subsequent "hits" is possible in a broken cable segment.

A number of optical techniques have also been developed over the years to try to address at least some of these issues. Johns Hopkins University Applied Physics Laboratory (JHU APL) has developed several optical techniques including the Light-Speed Hitpoint Sensor (LSHS). Although this system is also a passive system, it is more complex and incapable of determining multiple hit-point locations once its single fiber is severed because of the architecture employed and its time of flight measurement can also be confused by multiple impact detections.

Another example of an optical system developed by JHU APL is the Blast Initiation Detector (BID). The BID detects the time of a collision by viewing the exterior of the surface. The BID is a high-speed instrument that detects rapid onset optical events. It has a wide field-of-view and uses high-temperature optical fibers that maintain their field-of-view and optical throughput during rapid heating that occurs during reentry into the earth's atmosphere.

JHU APL also developed the Planar Optical Penetration Sensors (POPS). The POPS sensor includes a sandwich of a transparent layer within two reflective layers, which in turn are within two opaque layers. An optical sensor structure includes a set of sensors positioned in respective planes, wherein at least two non-parallel optical sensors are used for each trajectory dimension of interest that differs from the primary direction of motion of the projectile and one additional optical sensor may be used for independent measurement of velocity attenuation.

Other fiber-optic based optical systems include ITT's Photonic Hit Indicator (PHI). The PHI is a fiber-optic grid that is designed to provide unique impact location indications for different flight test targets.

While these hit-point sensor systems accomplish their intended purpose of detecting or locating energetic impacts on a surface of interest, they are incapable of detecting multiple near simultaneous hit-points. Another feature of these systems, when used in high-velocity impact and explosives testing, is that the data must be retrieved and stored or transmitted in a very short time period. The particular amount of data to be stored, or transmitted, depends on the technique but is limited by the speed of preprocessing needed to reduce more complex raw data and the bandwidth of the data recording or telemetry system in use. It is therefore desirable to minimize the amount of data collected, processed, and transmitted to support determining the location of multiple energetic penetrations of a surface or volume and the subsequent progression of that penetration and damage in time.

The present invention is aimed at providing a sensor capable of locating multiple energetic penetrations of a surface or volume and recording the progression of that penetration and/or subsequent damage in time. It also is very data efficient and requires only a minimum of data throughput to provide these features, and therefore inherently provides higher speed recording of the events over that of currently available systems.

DETAILED DESCRIPTION OF THE DRAWINGS

The primary purpose of the invention is to detect, count, locate, characterize, telemeter and record one or more near simultaneous hit or contact indicating events with sufficiently high kinematic energy to register as a "hit". The secondary purpose of the invention is to do this with a minimum of complexity, a low SWAP (Size, Weight and Power), a low cost, a low implementation impact, with minimal spatial interference and robust, elegant and reliable operation.

Figure 1:
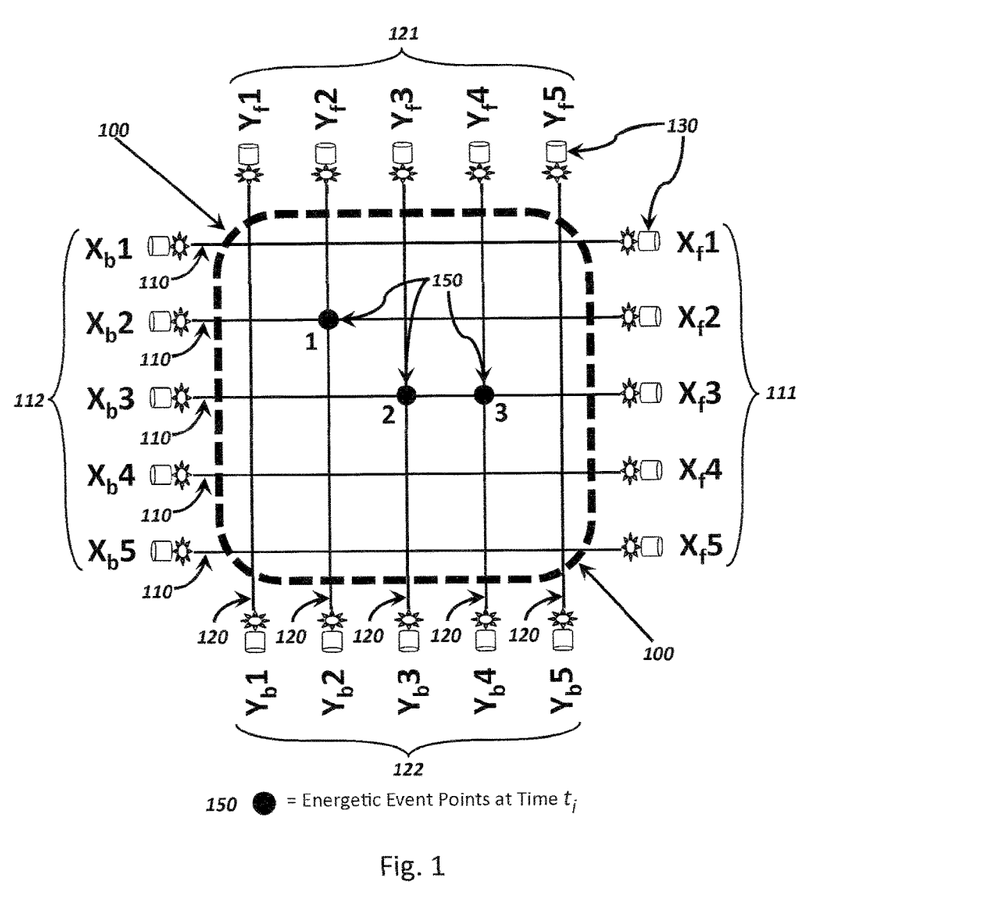
FIG. 1 shows a top down view of a first simple embodiment of the invention, illustrating a 2-dimensional rectilinear grid of nominally passive sensing lines and corresponding signal receivers at their ends according to the principles disclosed herein. Also shown are unique labels for said signal receivers, and three representative energetic impact points.

FIG. 1 shows a top down view of a first 2-dimensional (hereafter "2D") planar embodiment of the invention. Item 100 is a representative target, test article or object (hereafter the "target") having a 2D surface from which hit or contact indications from impacting or contacting objects or bodies (hereafter "impactors" or "contacts" respectively) are desired. In one application of the invention, target 100 could be a witness panel or plate for collecting warhead ballistic fragments. In a second application of the invention, target 100 could be a section of vehicle armor plating placed for testing of its protection capability. In a third application of the invention, target 100 could be one small section of a larger vehicle or body of particular interest. In a fourth application of the invention, target 100 could be the outer surface of a body or vehicle for which sensing of contact with another body or vehicle is desired. In general then, the invention has use in any application where it is desirable to sense and characterize impacts and/or contacts.

Although the focus of the invention is to register the impact or contact of moving impinging objects or bodies upon a locally stationary target, it is obvious that by reciprocity, the same invention is capable of registering the impact or contact of a moving target impinging on one or more locally stationary objects or bodies. In this way, the invention can be used to measure objects or bodies impinging on the target, or conversely measure the target impinging on objects or bodies.

FIG. 1 also shows a 2D rectilinear grid of the invention comprising a first set of substantially parallel, separate and discrete horizontal sensing or detection lines 110 (hereafter "sensing lines") identified with "X" labels 111 and 112, substantially perpendicular to and crisscrossing with a second set of substantially parallel vertical sensing lines 120 (also hereafter "sensing lines") identified with "Y" labels 121 and 122. Alternatively, the horizontal or said vertical sensing lines may be disposed at any alternative angle other than either horizontal or vertical, as long as the two sets of sensing lines are mutually and substantially independent of each other, forming a skewed or curvilinear coordinate system where the coordinate surfaces are not necessarily orthogonal. The substantially parallel sensing lines are spaced close enough to each other to resolve impacts and contacts to the resolution desired for the measurement of said impacts and contacts, but far enough from each other to minimize the total number of sensing lines in order to minimize complexity and cost. As shown, the grid may be configured as a plane that may be flat, or curved to fit on any curved surface.

It should be noted that although the current invention anticipates a 2D layout of two substantially perpendicular sets of crisscrossing sensing lines, this is not an overt limitation of the invention. In cases where only one dimensional (here after "1D") resolution is needed of impacts or contacts (such might be the case against a cylindrical target), then only one set of substantially parallel horizontal sensing lines may need to be employed, or alternatively only one subset of substantially parallel vertical sensing lines may need to be employed. Alternatively, three or more sets of substantially parallel sensing lines might be employed at mutual angles less than 90 degrees such as 45 degrees or 30 degrees, to provide redundancy and additional correlated measurements. In cases where a three dimensional (hereafter "3D") resolution is needed of impacts or contacts (a volumetric sensing application), then multiple spaced layers or planes of the aforementioned 2D grid of signal lines may be employed to provide a 3D impact and contact sensing capability, as will be disclosed further subsequently. As noted, such planes may be flat or curved as required.

The first key function of the sensing lines is to convert (transduce) some amount of mechanical energy, which in the case where optical fibers are used may be photonic energy of any frequency developed by a highly energetic event, such as infrared, visible or any other usable light frequency, which energy being deposited by the impactor or contact at time of contact into the most proximate sensing line, thereby forming a signal within the sensing line that can propagate down both opposing directions of the sensing line. In a typical instance, an optical fiber is severed by the impact, and the described light energy is deposited into each end of a severed cable. In this way the invention is considered completely passive, as it requires no active source of other energy to produce the signal. As such, no predetermined signal is injected into the detection lines forming one or more grids. The second key function of the said sensing lines is to propagate the signal at a sufficiently high velocity to support the requirements of the measurements. For example, in highly energetic explosive or high velocity impact type applications, a signal propagation velocity near the speed of light in a fiber optic cable is highly desirable before catastrophic disassembly of the target and the grid of sensing lines occurs. In slower kinematic scenarios, a sonic velocity of signal propagation may be sufficient to support the requirements of the measurements.

In a first embodiment of the invention, and as noted, the sensing lines could be optical fibers. However, the invention is not limited to only these types of sensing lines. Any physical mechanism that can transduce the local impact or contact energy deposited by an impactor or contact into a signal on the sensing line, that can then be transmitted along the sensing line, may be used. Examples of candidate alternative sensing lines include but are not limited to conductive wires, matched pairs of conductive wires (more typically used in an active sensing configuration), RF transmission lines (TL), pneumatic tubes, hydraulic tubes, or sonic conduits (either tubes to carry sound or solid material lines with ability to carry sound waves), to name a few.

Although the focus of the invention is on sensing lines that have inherent integral transduction capability, the invention does not preclude the use of means to amplify or further localize said transduction, such as discrete transducers either in-line with (in series with) or tapped into and along (in parallel with) the sensing line at sufficiently close spacings to ensure a desired measurement accuracy and resolution of the desired impactors or contacts. Examples of candidate alternative amplifying means for sensing lines include but are not limited to pyro-photonic enhancers (materials that burn or glow upon impact or contact to add more light for sensing) and conductive wires or RF TLs with integral piezoelectric material (to convert and amplify mechanical energy to a measurable signal thence carried on the wires or RF TLs). In some embodiments, the piezoelectric material may be integrated into the cladding of fiber optic cables. in other embodiments, ambient or external light may be used to generate an optical signal. Here, when a fiber optic cable is broken, ends of the broken fiber become available to admit light into both sides or strands of the fiber-optic cable on each side of the break. In instances where sufficient heat is generated by an impact, glass or plastic strands of the broken ends of the fiber-optic cable may fuse and form a ball or spherical shape at the broken ends, which serve as a lens to amplify and transmit light into respective ends and respective portions of the broken cable.

The sensing lines 110 and 120 are substantially but not necessarily fully conformal to the external (top) surface of target 100. The invention admits the possibility of a standoff spacing (not shown) between the external surface of target 100 and sensing lines 110 and 120. Such standoff spacing may serve a special purpose in a given application but is generally to be minimized in order to maximize location accuracy and adherence of the sensing lines to the target during the impact events. However, there can be reason and benefit to such a standoff. One benefit of a standoff may be for electrical, optical or mechanical isolation. Another benefit of a standoff may be the introduction of a suitable adhesive between the target's external (top) surface and the sensing lines to keep them firmly in place. In most cases such a standoff will be limited to the thickness of the adhesive and introduces little issue due to the small thickness of most adhesive layers.

A further benefit of a standoff may be to introduce a "boot" or "sleeve" over an external surface of the target, with depressions therein for the mechanical retention of the sensing lines, perhaps augmented with an adhesive to further retain the sensing lines. In other embodiments, grooves may be cut into a surface of the target itself, and within which the sensing fibers or conductors are laid and maintained in place by adhesive or an outer covering. An additional benefit of a standoff may be for the introduction of an impact transduction amplifier material. In the case of optical fiber sensing lines, such a material could be a pyro-optic material that produces copious additional light when subject to the energy imparted by an impactor or contact that in turn increases the signal in the fiber optic over that which might be realized otherwise. In the case of electric wires or RF lines, such a material could be a piezoelectric material that produces a substantial voltage when subject to the energy imparted by an impactor or contact that in turn increases the signal in the wire over that which might be realized otherwise. Similar approaches might be taken for other types of sensing lines, the key attribute being to help transduce and amplify the impactor or contact mechanical energy from the actual contact into signal energy in the appropriate sensing lines corresponding to the locality of the impact or contact.

The sensing lines 110 and 120 may be mechanically pulled or wrapped onto the target using only physical tension for retention. Alternatively, an adhesive may be applied to the external surface of the target before the sensing lines are laid or wrapped thereto in order to secure the sensing lines in place. In some instances, a flexible adhesive would be used, such as a silicone adhesive or the like, to allow for expansion and contraction of the target due to heating and cooling, such as would be found in a projectile or aerodynamic body. A further alternative is to apply adhesive directly to the sensing lines themselves before laid or wrapped onto the target, or to simply "paint" or "spray" adhesive onto the combination of target and sensing lines after they have been laid or wrapped onto the target. A further option could be to embed the sensing lines into a conformal "sock" that is applied over the external surface of the target, or to knit or otherwise form such a sock from the sensing lines themselves into an integral sock for similar application over the target application.

It should be noted that although the instantiation described above is focused on application of the sensing lines 110 and 120 to the exterior (top) surface of the target 100, this does not preclude applying all the teachings herein to employment of the sensing lines 110 and 120, or a duplicate set of similar sensing lines, to the internal (bottom) surface of the target 100. Such an application of the invention would be useful for detecting, localizing and characterizing spalling from impacts, or for detecting, localizing and characterizing ricocheting debris anterior to the target or within a target.

Once an impactor or contact transduces energy into one or more sensing lines 110 and 120, the resultant signal continues along the sensing lines nominally in both directions of each line until the signal has propagated to the ends of the sensing lines at signal receivers 130, one on each end of each said sensing line 110 and 120, and further enumerated by 111, 112, 121, and 122. As such, a plurality of separate and discrete signals indicative of a highly energetic event are detected at each end of respective separate and discrete detection lines. In the case of other types of sensing lines using different phenomenologies, there may be correspondingly different receivers configured and used for signal receivers for those types of sensing lines.

The set of sensing lines 110 and 120 form a coordinate system, which is unique and adjacent to all points on the surface of target 100. Each sensing line within the set of labeled "X" sensing lines 110 and the crossing set of labeled "Y" sensing lines 120 are further labeled either with subscripts "f" or "b" denoting the frontend and backend of the said sensing lines, respectively. Each sensing line within the set of labeled "X" sensing lines 110 is additionally further labeled with an appended number unique to that specific sensing line in the set 110, and likewise for the set of labeled "Y" sensing lines 120. In this manner, the labeling provides unique identification of each end of each individual sensing line, the orientation and coordinate direction of each sensing line, and through the unique identification and a priori knowledge of the layout of all sensing lines, the specific coordinate points covered by each sensing line within the coordinate system defined by all the sensing lines.

When an energetic penetration event or contact occurs at a point, or points, on the surface of target 100, some of the energy of the impact or contact will transfer to the target 100 and one or more of each of the nearest sensing lines 110 and 120. The transferred energy will transduce a signal into one or more of the proximate sensing lines. In the case of a high energy impact, the transduction likely manifests as a damage center in target 100 that spreads until it reaches a sensing line.

In an embodiment where the sensing line is an optical fiber, it could be of either the single mode or multimode variety, with multimode potentially preferred due to its ability to carry a multiplicity of light frequencies (actual selection will depend on the detailed specifics of the application, its goals, and requirements). The energy of the propagating damage center causes penetration of the optical fiber. The energetic penetration of the optical fiber produces a high temperature as well as high pressure and density, which conspire to both generate light and couple thermal radiation into the fiber. The light and thermal energy thus generated by the penetration of the optical fiber includes ultraviolet, visible, and infrared radiation of differing intensities which then propagate down both directions of the optical fiber. Signal receivers or detectors 130, one at each end of the sensing line, then convert the signal from the sensing line into a readily employable electrical output signal.

For an optical fiber based embodiment, the signal receivers 130 further comprise high speed opto-electronic Commercial-Off-The-Shelf (COTS) photo-detectors not unlike those used in the telecommunications industry. One such opto-electronic receiver 130 is mated to each end of each of the optical fibers 110 and 120 at both the frontends 111 and 121 and backends 112 and 122 to provide reception and conversion of any optical signal transduced into the optical fibers into electrical signals that can be easily read, conditioned and recorded. Each fiber optic sensing line and the optical receiver may be mechanically secured to a mounting block for mechanical attachment and subsequent electrical connectivity to the post detection processing elements.

During an impact between a target 100 and another body, the closest optical fibers to an energetic penetration will be severed and others nearby possibly damaged. The process of severing or damaging the optical fibers will produce an optical signal in those specific proximate optical fibers thusly severed or damaged. This optical signal will travel in both directions of each severed or damaged optical fiber, and then this optical signal will be converted to an electrical signal by the optical receivers at the ends of the optical fibers. Thus, the same optical signal indicative of an energetic event will be detected by detectors at each end of a discrete severed cable. Other optical fibers will remain dark, since optical fibers have a very high isolation to exterior illumination, and each receiver at respective ends of each discrete cable will receive the same signal indicating an unbroken cable.

It should be noted that in addition to the optical receivers described above, additional optical receivers (not shown) might be added midway along each optical fiber through the use of optical couplers disposed midway along each optical fiber. This would serve to effectively split the optical fiber into two segments, each with a substantially similar maximum number of hit indications, thereby doubling the total number of unambiguous hits that could be recorded by the system. A similar benefit is had by splitting each optical fiber midway and adding two additional optical receivers (one for each end of each new segment), but this requires twice again as many optical receivers and increases complexity and cost. This increases the hit count capability of the system as will be further disclosed.

In some embodiments, a clock pulse generator is provided to provide a train of clock pulses that are used to constantly monitor each end of each separate and discrete cable. Here, during each clock pulse, the state of each end of each discrete cable of the grid or grids is observed and possibly recorded, at least temporarily as will be explained. In the instance where a cable is unbroken, one binary value will be assigned to the unbroken state, and the other binary value will be assigned to the changed state indicating occurrence of a highly energetic event. As such, during each clock pulse, many such binary values will be collected. These values may be recorded on site, or transmitted as they occur to a remote location for analysis.

To illustrate the operation of the invention, by way of example, if optical fiber X2 in FIG. 1 is penetrated somewhere along its length by an energetic event, the optical receivers at Xb2 and Xf2 both respond to the incident light by changing their state and generate electrical signals which are recorded as a binary "1" pair from the optical receivers. These are subsequently time stamped in relation to the clock pulses or any other timekeeping method, when the electrical signal from a photodiode or other light sensing receiver surpasses a minimum voltage threshold, the threshold selected to be above an ambient noise level from the optical receivers, but below a level expected for an impact event of interest. At the same time an impact severs or disturbs any of the optical fibers, all other optical receivers connected to unsevered or undisturbed fibers or conductors thusly record a binary "0" and an associated time stamp, providing many time-aligned signals during each clock pulse. Note that the time stamp can be implied, such as by a signal receiver registering a binary "1" or binary "0" on each of many sequential sampling clock cycles, each clock cycle serving to time stamp the data by its sequential relation relative to all other clock cycles.

As the damage progresses, a second optical fiber may be eventually severed, for example Y2 with detections at optical receivers Yb2 and Yf2 in FIG. 1. These optical receivers generate subsequent signals which are recorded as a binary "1" pair and time stamped accordingly. These two pairs of binary numbers now locate an intersection where two detection lines cross and about which the initial event occurred; the point labeled "1" in FIG. 1. Other subsequent impacts produce indications at other intersections 150.

The resolution of the exact location of the initial energetic penetration of the surface of target 100 depends on the fineness, or spacing, of the "X-Y" grid (number of optical fibers per unit area) and the sequential timing of subsequent optical fiber penetrations by impactors. Ideally, recorded detections along a given "X" sensing line happen at or nearly at the same time as detections on the "Y" sensing line corresponding to the same impact event as caused the "X" sensing line detection, so as to correlate the two detections into a resolved "X-Y" position on the grid. Algorithms easily crafted by one skilled in the art resolve any correlating events that "straddle" the edges of temporal correlation gates and aid in computing the centroid of the spreading damage as a function of time to improve estimates of the initial energetic event location when the "X" and "Y" correlations are not perfect.

Figure 2:
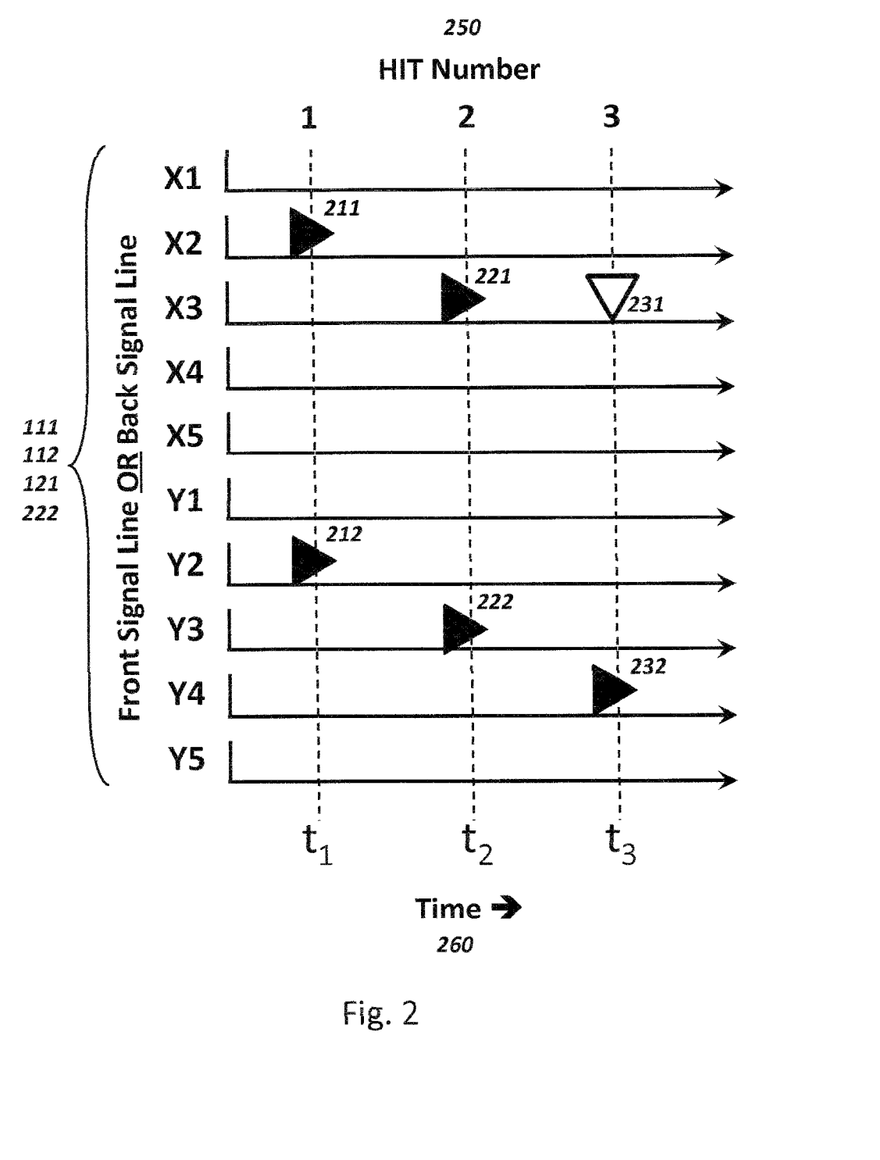
FIG. 2 shows a detection time history plot for the aforementioned three representative energetic impact points, showing the relative timing of their detections in the sensing lines proximate to their impact locations and how these are temporally correlated to resolve an "X", "Y" and potentially also "Z" location of impact on the target.

FIGS. 1 and 2 together illustrate the multiple hit detection capability of the present invention. Assume that at time 260 with t=t1, an energetic object impacts area "1" of 150 shown as Hit Number 1 at 250 in FIG. 2, and the resulting impact generates an energetic penetration of the optical fibers X2 and Y2. This event is detected optically by the detectors located at Xf2, Xb2, Yf2, and Yb2, and for clarity are logically "OR"ed together and shown with dark filled in triangles in the detection time history plot of FIG. 2 at 211 and 212 for X and Y respectively. Note that there is no complex timing required in order to perceive the location of the impact. The only requirement is that the two signals at 211 and 212 correlate in time. Given the much faster speed of light (even in an optical fiber) versus the speed of the impact dynamics, with a suitably timed and commonly available clock cycle rate on the order of a microsecond (1 MHz sampling frequency), such correlation is automatically provided in a very simple and straightforward way through simple logical AND gating of latching comparator outputs which temporarily store the changed state indicative of a broken cable. Straightforward algorithms easily crafted by one skilled in the art accommodate the case when correlation detections straddle detection bins or gates.

Likewise, further assume that at time t=t2 (where t2>t1) a second energetic event generates a penetration that is seen by the detectors located at Xf3, Xb3, Yf3, and Yb3 and shown with dark filled in triangles in the detection time history plot of FIG. 2 at 221 and 222 for X and Y respectively. The dark filled in triangles point to the right to indicate that both the front and the back optical receivers received an optical signal from the attached optical fiber.

Lastly, consider a third energetic impact event at time t=t3 (where t3>t2>t1). Even though the X3 fiber has already been severed from the impact at time t2, and cannot be seen by the detector at Xb3, the event is still detected at Xf3, Yf4, and Yb4, wherein it is shown with a non-filled downward pointing triangle in the detection time history plot of FIG. 2 at 231 for X, and a dark filled in right pointing triangle in the detection time history plot of FIG. 2 at 232 for Y. This is an advantage over current impact or hit-point detection systems in that it allows a multiple hit recording capability not previously available from a destructive energetic event. Note that even though in FIG. 2 the inputs are logically "AND"ed together to simplify the illustration of operation, in truth the recorded data includes the actual recordings of outputs from optical receivers at Xf3, Yf4, and Yb4 so there is no ambiguity as to where the hit occurred.

Figure 3:
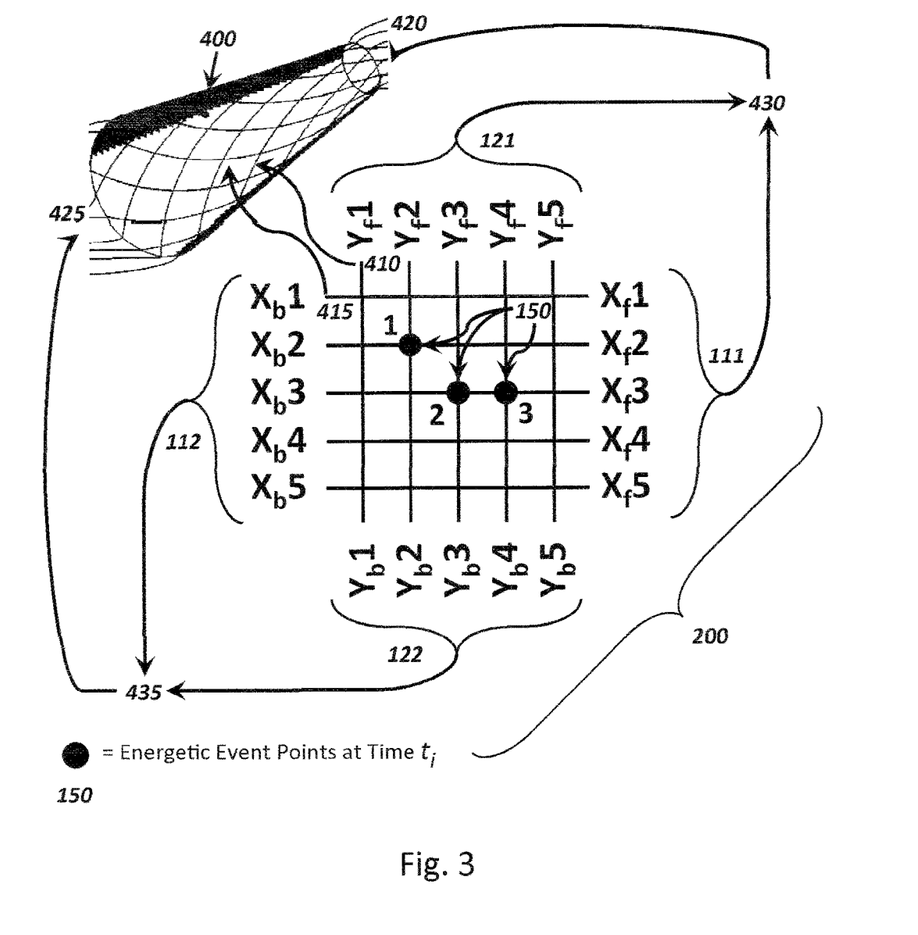
FIG. 3 shows how the 2-dimensional rectilinear grid of FIG. 1 can be wrapped about a target body of revolution to form a curvilinear grid on the surface of the target, and how the signal receivers are managed at the forward and aft positions on said target.

FIG. 3 illustrates the creation of an alternate embodiment of the invention wherein the rectilinear grid 200 described to this point is wrapped with a suitable curvilinear transformation about a three dimensional (hereafter "3D") target 400, resulting in a pseudo orthogonal grid of sensing lines 110 and 120. When thusly applied, first sets of signal receivers 111, 121 at the first end of the first and second set of crossed detection lines, are bundled together into receiver block 430 then located on the top end 420 of 3D target 400. Similarly then also, second sets of signal receivers 112, 122 at the second end of the first and second set of detection lines, are bundled together into receiver block 435 located on the bottom end 425 of 3D target 400. Note that operation of the grid is substantially the same as described previously, but now the exact [X,Y] geometric positions of the sensing line crossings map to the new coordinate system [X', Y', Z'] of 3D target 400. The specific mapping to use will depend on the specific shape and size of the 3D target 400, but is easily performed by one skilled in the art of 3D trigonometry and 3D geometry. Through this transformation, impacts or contacts are first registered on the grid 200, and thence transformed to a specific 3D point in space corresponding to the point on the surface of the 3D target 400 where the impact or contact occurred.

Figure 4:
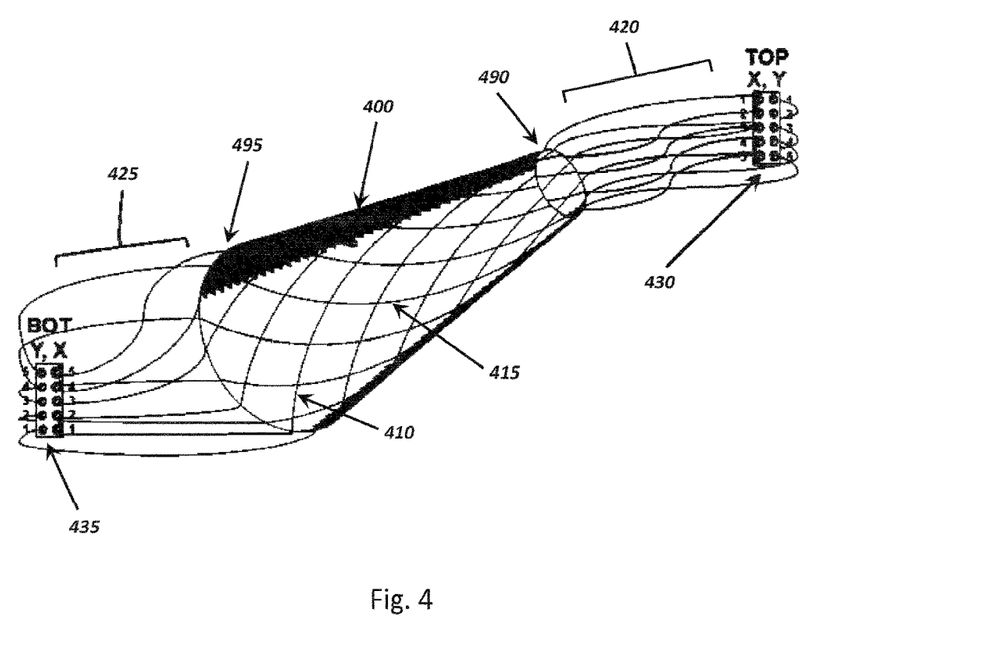
FIG. 4 shows the core components of the invention comprising a representative target or test article, a 2-dimensional grid of counter rotating helical wraps of sensing lines on a surface of the target or test article, top and bottom bundles of continuations of said signal lines, and top and bottom signal receiver blocks for electrically receiving signals from the sensing lines and converting them to electrical signals. The resulting sensor can provide a pseudo 3-dimensional volume sensing capable of measuring penetrations and/or hot-spot energetic events originating from within or without of the given volume.

FIG. 4 shows the core components of the new alternate embodiment just created by the aforedescribed wrapping of the grid about 3D target 400. Target 400 is a representative target, test article or object for which hit indications from impacting objects or bodies (here after "impactors") are desired. Target 400 will always have an external surface between some forward extent and forward facing surface 490 and some rearward extent and rear facing surface 495 which is of most interest because incident impactors most often arrive from a location external to an external surface of the target (hereafter "external impactors") and incident upon it. However, this does not preclude the possibility that alternatively, impactors might arrive from internal to the target (internal impactors). These internal impactors might manifest as "pass through" external impactors which impact the external surface of and enter into one external surface of the target (hereafter the "incident side"), thence passing through the target and arriving seemingly from inside the target before exiting the opposite side of the target (hereafter the "exitent side"). Additionally, internal impactors may manifest when an internal explosion, rupture or other energetic event might occur somewhere within the physical envelope of the target defined by the external surface.

In the evolution of the event to be measured, external impactors may impact the external surface of said target, or similarly internal impactors may impact the internal surface of the target should there be an internal surface. In the later case, said internal impactors will, if energetic enough, pierce the internal surface of target from within the target and either deposit energy within the material between the internal and external surfaces, or breach the external surface and potentially exit the target. In either case there is a substantial kinetic energy associated with the impactors, which when incident on the internal or external surface (either from without or from within) will deposit a considerable amount of energy into interstitial material, which is indicative of the kind of hit the invention wishes to measure the presence, location, and characteristics of.

Returning to FIG. 4, the sensing lines 410 and 415 are disposed in the grid substantially conformal to the external surface of the target, the grid given by a substantially curvilinear arrangement when employed on bodies of rotation such as cylinders, conics, ogives and similar three dimensional convex surfaces, as shown in FIG. 4. To form the grid on such curvilinear surfaces, sensing lines 415 are wrapped in a clockwise (counterclockwise) helix like manner, and sensing lines 410 are wrapped in a counterclockwise (clockwise) helix like manner. The wrap rate (i.e. number of turns about the longitudinal axis of the body of rotation per unit length along the longitudinal axis of the body of rotation) is nominally the same for both sensing lines 410 and 415 to ease subsequent computations of impactor location unless there is other alternative reason to not do so, which can be easily accommodated in the embodiment if needed. The wrap rate is also selected such that the maximum spacing between the sensing lines, particularly at a larger diameter end of a body of rotation, meets the desired spatial measurement resolution requirements for the application.

It should be noted that although the embodiment described above is focused on application of the sensing lines 410 and 415 to the exterior surface of the target due to ease of access and related favorable attributes, this does not preclude applying all the teachings above to application of the sensing lines 410 and 415 to one or more internal or interior surfaces within the target. The interior of an aero shell is one such possible interior application. Although the signature modification from application of the invention to an external surface is small, application to the inner surface of the aero shell might benefit an impactor measurement by ensuring that the sensing lines contributed absolutely no externally visible signature modification to the target's signature. Alternatively, it may be desirable to apply the invention independently to individual subsystems or component enclosures (typically replaceable units) internal to the target. This then would permit detailed insight into the mechanical dynamics occurring within the body of a target upon exposure to either external or internal impactors.

Once an impactor transduces energy into sensing lines 410 and 415, the resultant signal continues along the sensing lines in both directions of each line having such signal until the signal has propagated to the ends of the target at 490 and 495. At that point the sensing lines continue but are nominally bundled into a forward sensing line bundle 420 and a rear sensing line bundle 425 which connect to a forward receiver block 430 and a rear receiver block 435 respectively. Note that the aforementioned "bundles" need not be physical tubular collections of sensing lines (although they can be), but could be instantiated as a linear or circumferentially disposed aggregation of sensing lines if, for example, the receiver block 430 and 435 were disposed along an interior circumference of the target such as pointed out by 490.

The forward receiver block 430 and a rear receiver block 435 contain signal receivers 130 that covert the signal on the sensing lines 410 and 415 into an electronic signal that can then be pre-processed appropriately for extraction of basic impactor information and subsequently telemeter the resulting data to local or remote recording and subsequent post processing. An additional function of the receiver block is to provide secure and reliable mechanical mounting of the signal receivers to the body of the target.

Note that this scheme can provide multiple hit detections even if the sensing line is severed by the impactor because the signal travels in both directions to nominally identical signal receivers on both ends of the sensing lines. However, once two impactors have severed the sensing line at two distinct locations on the same sensing line, the middle section of line between the severed locations will no longer be able to provide hit indications. But sections of sensing line still connected to a receiver on either of the original two ends of the sensing line will still be able to detect hits. Although this presents a limitation of the system with respect to the inoperable sensing line section between two same line severed locations, the system can be designed to achieve any level of performance desired by dividing the length of the sensing line up into multiple sections of paired receivers.

For example, by shortening the sensing lines in FIG. 4 to about half the length shown, then they will then span from 400 to 495 instead of from 490 to 495. Then a similar set of sensing lines and receivers of about the same length can be set to span from 490 to 400, thus again fully covering the whole length of the target. Now however, each set individually, either from 490 to 400 or 400 to 495, requires two severed locations before hits are missed. Since the length of the severed middle section of each sensing line will be smaller by on average half what it was before, on average the system can measure twice as many hits without missing any hits with the same reliability as before. Again, any hits between the receivers and the first severed locations will still be able to detect hits regardless. Since hits tend to happen first near a first aimpoint usually near the center of the target, there is a good probability of not missing many hits even without the multiple receiver and sensing line section approach just described, and an even better probability with it. Sensing Line couplers may be used in lieu of fully cutting and inserting signal receivers, and in either case the sensing lines may be further subdivided as many times as needed to achieve any level of hit detection resolution performance desired.

Figure 5:
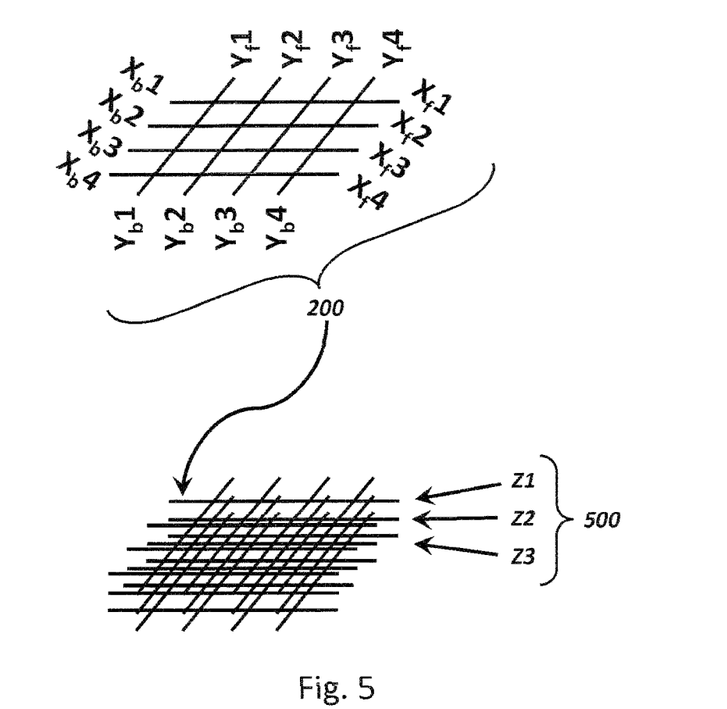
FIG. 5 shows a manner in which more than one rectilinear grid of sensing lines and associated signal receivers, may be stacked, either with or without interstitial standoffs from each other to create a comparatively thin but 3-dimensional sensor according to the principles disclosed herein that provides additional information such as direction of incidence and rate of progression through the thickness of the sensor grid.

FIG. 5 shows a perspective view of a 3D embodiment of the invention for a multiple energetic penetration and damage progression sensor. In this embodiment, a plurality of the previously described 2D grid embodiments as shown in FIG. 1, are. stacked atop each other in a substantially perpendicular direction to the plane of the grid, thereby providing a "Z" measurement direction by the given stack numbers 500. This embodiment is capable of measuring partial penetrations, the depth of penetration, the rate of penetration and the direction of penetration, to with originating from within or without of the given volume. This approach can also be used to increase the reliability of the system by providing multiple substantially overlapping grids arranged in corresponding planes, or it may, by offsetting each grid by a suitable fraction of the grid spacing, thereby enabling instantiation of a denser grid spacing without having to rework the entire grid. This may be of use if the sensing line grids are mass-produced into a standard layout but occasional testing requirements require denser measurements.

Figure 6:
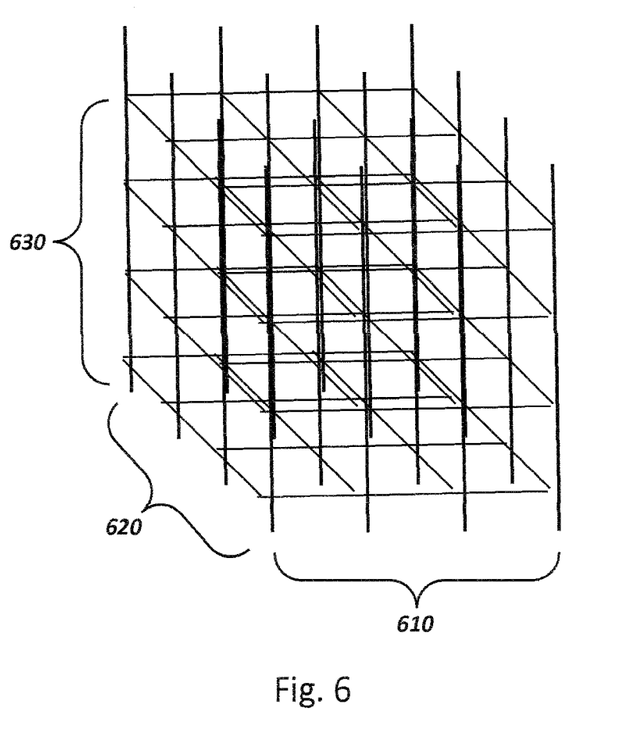
FIG. 6 shows an expansion of the embodiment in FIG. 5 allowing for full 3-dimensional sensing in all dimensions and with potentially liquid and cast formable target materials and shapes.

FIG. 6 shows a further embodiment of the a multiple energetic penetration and damage progression sensor in a full 3D "cubic" sensing line grid with "X" (610), "Y" (620), and "Z" (630) sensing lines. This embodiment of the present invention is also measuring partial penetrations, the depth of penetration, the rate of penetration and the direction of penetration to with originating from within or without of the given volume. Its instantiation could be by way of sandwiching 2D grid layers of sensing lines in the "X"-"Y" plane between layers of target material similarly oriented, the layers of target material having holes aligned in the "Z" dimension when they are co-aligned, so as to admit the insertion of linear sensing lines into the body of the whole stack in the remaining "Z" direction. Alternatively, the cubic grid of sensing lines could be pre-suspended and the space between sensing lines filled in with a liquid target material. If one is interested in aqueous target experiments, then the fill material could be water or any other liquid of experimental interest (oil, gasoline, chemicals, etc.). Alternatively, the liquid material could be one that hardens into a solid with a suitable curing time and with a suitable supporting casting form that can be made into any shape of target desired.

Figure 7:
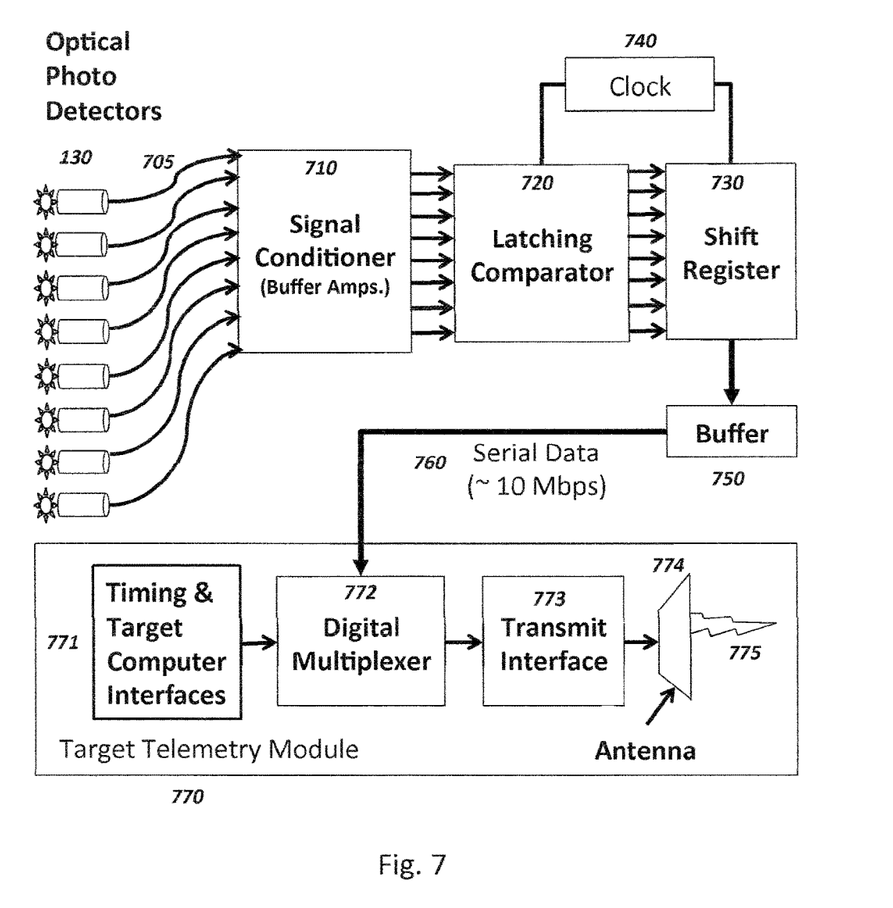
FIG. 7 shows a representative block diagram embodiment of the supporting electronics needed to register, collect, correlate, format, transfer, record, and potentially transmit the sensor data to a safe downlink station.

FIG. 7 shows the basic post detection processing elements needed to instantiate the invention. The signal receivers 130 (which are nominally optical photo detectors in an embodiment employing optical fibers for the sensing lines) are each connected to an individual channelized small, simple signal conditioning circuit 710. This circuit is usually quite simple and serves only to provide impedance matching, debouncing and oscillation suppression, and to provide a degree of signal amplification and buffering to ensure good Signal to Noise Ratio (SNR), minimization of false detections, and isolation and protection of the front end electronics from electromagnetic interference (EMI), discharge (EMD) and electrical damage.

The conditioned and amplified signals are then fed to a Latching Comparator 720, one per signal receiver 130, and subsequently to Signal Conditioner 710. Comparator 720 is triggered by a Clock signal provided by a clock 740, which as noted may run as fast as 1 mHz or faster for extremely fast events, or slower for slower events. The Latching Comparator trips and latches an input signal when its signal level (usually a voltage but potentially a current) exceeds a predetermined comparative signal level selected to minimize false exceedances while maximizing sensitivity to detection of events. As such, a threshold value is integrated into signal conditioner 710, such that an input from a photodiode or the like must exceed in order for a respective output to be provided from signal conditioner 710. Such a threshold, as noted above, would be selected to be above any ambient or anticipated noise levels, but sufficiently low that impact events that sever or disturb a conductor or fiber of the network are detected. The action of the Clock and Latching Comparator together serve to act as a temporal correlator. As noted, the Clock rate is selected to be fast enough so that individual latched data samples have a low probability of including multiple simultaneous hits on the same sensing lines. This then determines the temporal resolution of the system. Because the Clock is related to the speed and frequency of impacts, and because the impacts are almost never truly coincident in time, the Clock rate can be set to a fairly reasonable value, such as 1 MHz, and still provide ample temporal resolution for most situations. If needed, the Clock rate can be increased, and high rate COTS Latching Comparators can support sample rates approaching or possibly exceeding 1 GHz or so as of this writing.

As there could be hundreds of signal receivers 130, data density is of paramount importance in order to convey the damage events as rapidly as possible during energetically destructive testing. The Latching Comparator 720 is extremely efficient at recording and temporarily storing the data, requiring only one bit for an event detection on each cycle of the clock. To capture the outputs (a binary "1" or "0") from the many signal receivers maybe a couple hundred or few hundred bits of each Clock cycle may be required.

Shift Register 730 is representative, by way of example only, of simple logic that would be programmed nominally into a Field Programmable Gate Array (FPGA) or similar programmable logic device in order to logically accumulate the sequentially latched signals and transfer them into a Buffer 750 awaiting more permanent storage, recording or transference. Shift register 730 and buffer 750 may also be regarded as temporary storage. Given the prior estimates for numbers of bits and clock rates, this buffer likely fills up at a rate of about 100 Mbps (Mega Bits Per Second). If more permanent on board data recording is provided, solid state memory easily supports much higher direct recording rates than this. However, where telemetry is used to transmit data to a remote location, data rates are usually much lower commensurate with 10/100 Base-T Ethernet 760 such as supported by the illustrated Target Telemetry Module 770. However, this is not deemed a problem even in short lived energetic events, since the majority of the most desired impactor information is collected in the first couple of hundred microseconds of the event, and this data will have seen its way through the Target Telemetry Module 770 and downlinked long before the entire system of FIG. 7 undergoes catastrophic deconstruction. And this does not even consider the possibility of using data compression to further increase the information density in the downloaded data. It is therefore seen that the invention also supports highly efficient information encoding for the impact and contact information desired.

In other embodiments, and as noted, a shift register may be used to initially record clocked data, but in the absence of a bit or bits indicating a "hit", the data in the shift register indicative of a non-hit may be simply shifted out of the registers and discarded. The occurrence of a received bit or bits indicating a "hit" in a first memory cell of the shift register would then set a flag to trigger recording or transmission of telemetry data, thus recording or transmitting data already in the shift register just prior to the "hit" and data subsequent to the "hit" until the system is destroyed or otherwise becomes non-functional. This would reduce the necessity of a long recording capability and perhaps simplify the system such that only data surrounding an impact is recorded or transmitted.

The present invention may be applied to a wide variety of surfaces and/or volume geometries which admits the surface application of sensing lines such as optical fibers, or, the immersion in and wrapping around or surrounding of a solid or liquid energetic material. It should be apparent to those skilled in the art that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

REFERENCES

1) U.S. Pat. No. 7,406,219, Jul. 29, 2008, Gauthier, Jr.
2) U.S. Pat. No. 4,781,056 November 1988 Noel et al.
3) U.S. Pat. No. 4,836,030 June 1989 Martin
4) U.S. Pat. No. 5,015,842 May 1991 Fradenburgh et al.
5) U.S. Pat. No. 5,072,110 December 1991 Lu et al.
6) U.S. Pat. No. 6,559,437 May 2003 Pope et al.
7) U.S. Pat. No. 7,189,959 March 2007 Morison et al.
8) 2004/0206187 October 2004 Williams
9) 2004/0256543 December 2004 Ishihara
10) 2006/0180380 August 2006 Munch et al.
11) 2006/0278240 December 2006 Spillman et al.
12) 2006/0291767 December 2006 Andrews et al.

Having thus disclosed our invention and the manner of its use, it should be apparent to those skilled in the relevant arts that incidental changes may be made thereto that fairly fall within the scope of the following appended claims, wherein we claim:

1. A method for closely detecting location of one or more highly energetic events on a body, said method comprising:
    associating a plurality of separate and discrete detection lines with at least a surface of said body,
    continuously detecting, during discrete detection increments of time, detection signals at each end of each detection line of said plurality of detection lines without injecting any signal into said plurality of detection lines, and obtaining detection signals from a respective said each end of each said detection line during each detection increment so that a plurality of separate and discrete time-aligned detection signals are obtained from respective ends of said plurality of detection lines during each said detection increment of time,
    severing or disturbing at least one said detection line by said highly energetic event,
    detecting energy of said highly energetic event through severed ends of at least one severed said detection line, changing a value of said at least one detection signal at said each end of said respective severed or disturbed at least one detection line,
    from said changed value, determining a location of said highly energetic event on said surface of said body in relation to location of said severed or disturbed said detection line.

2. The method as set forth in claim 1 further comprising arranging said plurality of detection lines so that a first set of said detection lines associated with said surface cross a second set of said detection lines associated with said surface, forming a coordinate pattern of said plurality of detection lines across said surface, and wherein said determining a location of said highly energetic event further comprises locating said highly energetic event on said surface of said body in relation to location where at least two severed or disturbed said detection lines of said first set of detection lines and said second set of said detection lines cross.

3. The method as set forth in claim 2 further comprising obtaining some of said plurality of separate and discrete detection signals from a respective first end of said first set of said detection lines, and obtaining others of said separate and discrete detection signals from a respective first end of said second set of detection lines, and obtaining the same said separate and discrete detection signals from a respective second end of said first set of said detection lines and a respective second end of said second set of detection lines when said detection lines of said first set and said second set are not severed or disturbed.

4. The method as set forth in claim 3 further comprising obtaining said some of said plurality of separate and discrete detection signals from said first end of said first set of said detection lines and obtaining said others of said separate and discrete detection signals from a respective first end of said second set of detection lines, and obtaining the same said separate and discrete detection signals from said respective second end of said first set of said detection lines and said respective second end of said second set of detection lines when at least some of said detection lines of said first set and said second set are severed once or disturbed by said highly energetic event, and determining location of said highly energetic event on said surface from location of an intersection of said severed or disturbed said detection lines of said first set and said second set.

5. The method of claim 4 wherein said associating said detection lines with a surface further comprises associating said first set of detection lines and said second set of detection lines with a generally elongated 3-dimensional surface wherein said first ends of said first set of detection lines and said first ends of said second set of detection lines are at one end of said generally elongated 3-dimensional surface, with a first set of said separate and discrete detection signals obtained from said first end of said first set of detection lines and said second set of detection lines, and said second ends of said first set of detection lines and said second ends of said second set of detection lines at an opposite end of said 3-dimensional surface, with a second set of said separate and discrete detection signals obtained from said second end of said first set of detection lines and said second end of said second set of detection lines.

6. The method as set forth in claim 2 further comprising detecting location of an additional highly energetic event along said at least one previously severed detection line by detecting a said changed value at one said end of a portion of said previously severed detection line.

7. The method as set forth in claim 6 wherein said associating a plurality of separate and discrete detection lines with at least a surface of said body further comprises putting said detection lines on said at least a surface of said body.

8. The method as set forth in claim 7 wherein said incrementally detecting during discrete detection increments of time further comprises providing a train of clock pulses, and recording a said detection signal at each respective end of each said detection line during discrete clock pulses of said train of clock pulses, thereby recording a train of time-aligned detection signals from said each end of each said detection line.

9. The method as set forth in claim 8 further comprising:
    at least temporarily storing said time-aligned detection signals for a predetermined period of time,
    discarding said temporarily stored time-aligned signals if no said highly energetic event occurs that severs or disturbs a said detection line during said predetermined period of time, or, saving said temporarily stored time-aligned detection signals if said highly energetic event occurs that severs or disturbs a said detection line during said predetermined period of time.

10. The method as set forth in claim 9 wherein said saving said temporarily stored time-aligned detection signals further comprises temporarily storing said time-aligned detection signals in a temporary memory, and when a said detection line is severed or disturbed during said predetermined period of time, transmitting said stored time-aligned detection signals to a remote location or permanently saving in a memory said time-aligned detection signals.

11. The method as set forth in claim 6 further comprising arranging said discrete and crossed said detection lines in a plurality of planes spaced apart from one another, and fixing said spaced-apart planes within a volume, for detecting progression of said highly energetic event through said volume.

12. The method as set forth in claim 2 wherein said detecting of detection signals further comprises assigning one of a binary "0" or "1" to indicate no severing or disturbance of said detection line, and assigning the other of said binary "0" or "1" to a changed said value indicative of a severed or disturbed said detection line.

13. The method as set forth in claim 12 further comprising determining location of said highly energetic event on said surface by comparing said binary "1" taken from said crossed at least two severed or disturbed said detection lines of said first set of detection lines and said second set of said detection lines with respect to said binary "0" taken from unsevered or undisturbed said detection lines.

14. The method as set forth in claim 1 further comprising using light guides for said detection lines, and detecting a flash of light from said highly energetic event in said severed ends of a severed said light guide, and detecting said flash of light at each end of said severed light guide.

15. An apparatus for detecting highly energetic events on a surface comprising:
   a plurality of separate and discrete detection lines on a surface of a body,
   a clock signal generator for generating a train of clock pulses,
   a detector connected to each end of each separate and discrete detection line, and responsive to said clock pulses, for passively obtaining a signal at each said end of each separate and discrete detection line during discrete clock pulses without injecting any predetermined detection signal into said detection lines, so that a plurality of time-aligned detection signals are passively obtained from each end of said plurality of separate and discrete detection signals during a respective clock pulse,
   when one or more of said detection lines are severed by a highly energetic event, determining location of said highly energetic event on said surface by detection of energy from said highly energetic event transmitted by severed ends of said severed detection lines.

16. Apparatus as set forth in claim 15 wherein said separate and discrete detection lines are arranged in a coordinate system wherein a first set of said separate and discrete detection lines are arranged generally parallel to each other and in one direction on said surface, and a second set of said separate and discrete detection lines are arranged generally parallel to each other and arranged on said surface to cross said separate and discrete detection lines of said first set of detection lines, forming intersections between said first set of detection lines and said second set of detection lines, with a discrete said detector connected to each end of each said detector line of said first set of detection lines and said second set of detection lines, and a signal processor connected to each said detector, said signal processor adapted to determine a location of said highly energetic event on said surface from location of at least one intersection of crossed and severed said detection lines of said first set and said second set, and time stamping at least one said clock pulse during which said highly energetic event occurs.

17. Apparatus as set forth in claim 16 further comprising adapting said signal processor to detect subsequent said highly energetic events by detecting energy from a following said highly energetic event transmitted to at least one said detector at a single end of a previously severed said detection line, and determining location of said following highly energetic event on said surface by location of a said intersection where a portion of at least one previously severed said detection line is connected to said detector.

18. Apparatus as set forth in claim 17 wherein said coordinate system is arranged as a plane, with a plurality of planes each having a respective said first set of separate and discrete detection lines and a respective second set of separate and discrete detection lines, said planes oriented in a volume to monitor progression of said highly energetic impact through said volume.

* * * * *